United States Patent [19]

Johnston et al.

[11] Patent Number: 5,112,609

[45] Date of Patent: *May 12, 1992

[54] ACIDIC FORMULATIONS OF T-PA

[75] Inventors: Michael D. Johnston, Beckenham, England; Henry Berger, Cary, N.C.

[73] Assignee: Burroughs Wellcome Co., Research Triangle Park, N.C.

[*] Notice: The portion of the term of this patent subsequent to Nov. 6, 2007 has been disclaimed.

[21] Appl. No.: 527,634

[22] Filed: May 21, 1990

Related U.S. Application Data

[63] Continuation of Ser. No. 862,774, May 13, 1986, abandoned.

[30] Foreign Application Priority Data

May 28, 1985 [GB] United Kingdom ............... 851358
Aug. 31, 1985 [GB] United Kingdom ............... 8521704

[51] Int. Cl.⁵ .................... A61K 37/547; C12N 9/50
[52] U.S. Cl. .................... 424/94.64; 514/822; 530/324; 435/212
[58] Field of Search ............ 424/94.64; 514/822; 530/324; 435/212

[56] References Cited

U.S. PATENT DOCUMENTS

| | | | |
|---|---|---|---|
| 3,998,947 | 12/1976 | D'Hinterland et al. | 424/101 |
| 4,505,893 | 3/1985 | Mori et al. | 424/94.64 |
| 4,568,544 | 2/1986 | Hasegawa et al. | 424/94.1 |
| 4,968,617 | 11/1990 | Johnston et al. | 435/212 |

FOREIGN PATENT DOCUMENTS

| | | |
|---|---|---|
| 0041766A2 | 12/1981 | European Pat. Off. |
| 93619 | 11/1983 | European Pat. Off. |
| 0100982 | 2/1984 | European Pat. Off. |
| 112122 | 6/1984 | European Pat. Off. |
| 123304 | 10/1984 | European Pat. Off. |
| 124613 | 11/1984 | European Pat. Off. |
| 156169 | 10/1985 | European Pat. Off. |
| 0217379A2 | 4/1987 | European Pat. Off. |
| 0217379 | 4/1987 | European Pat. Off. |
| 2051075A | 1/1981 | United Kingdom |
| 2138824B | 12/1986 | United Kingdom |

8303101 9/1983 World Int. Prop. O.

OTHER PUBLICATIONS

Rote Liste, 1985*.
J. Biol. Chem., 254(6) pp. 1998-2003, 1979, Binder, et al.
Rijken et al. J. Biol. Chem., 256(13), 7035-7041, 1981.
Yukiyoshi Hamaguchi, Mie Medical Journal, vol. XXXIII, No. 1, 1983, Partial Purification and Properties of Tissue-Type Plasminogen Activator From Nasal and Maxillary Mucosae.
Rijken, et al., The Journal of Biological Chemistry, vol. 256, No. 13, Jul. 10, 1981, pp. 7035-7041, Purification and Characterization of the Plasminogen Activator Secreted by Human Melanoma Cells in Culture.
Binder, et al., The Journal of Biological Chemistry, vol. 254, No. 6, Mar. 25, 1979, pp. 1998-2003, Purification and Characterization of Human Vascular Plasminogen Activator Derived from Blood Vessel Perfusates.
Welmar, et al., The Lancet, Nov. 7, 1981, Preliminary Communication, pp. 1018-1020, Specific Lysis of an Iliofemoral Thrombus by Administration of Extrinsic (Tissue-Type) Plasminogen Activator.
Abstract-Preparative Biochemistry, 12(4), pp. 297-305, (1982).
Remington's Pharmaceutical Sciences, Fifteenth Edition (1975), pp. 273-274.
Dano et al., Biochimica et Biophysica Acta 613(1980) 542-555.
Camiolo et al., cited in Biological Abstracts 76(2):883 Ref. No. 8252 1982.
Wilson et al., Chem. Abstracts, vol. 92:144679a, 1980.
Vetterlein et al., Chem. Abstracts, vol. 90:135631k 1979.
Hamaguchi, Mie Medical Journal, vol. XXXIII, No. 1, 1983, pp. 57 and 66 to 67, Partial Purification and Properties of Tissue-Type Plaminogen Activator from Nasal and Maxillary Mucosae.

Primary Examiner—Jacqueline Stone
Attorney, Agent, or Firm—Donald Brown; Lawrence A. Nielsen

[57] ABSTRACT

An aqueous parenteral solution of tissue-plasminogen activator, in which the pH is from 2 to 5.

31 Claims, 3 Drawing Sheets

Ser Tyr Gln Val Ile Cys Arg Asp Glu Lys Thr Gln Met Ile Tyr Gln Gln His Gln Ser
1

Trp Leu Arg Pro Val Leu Arg Ser Asn Arg Val Glu Tyr Cys Trp Cys Asn Ser Gly

Arg Ala Gln Cys His Ser Val Pro Val Lys Ser Cys Ser Glu Pro Arg Cys Phe Asn
50

Gly Gly Thr Cys Gln Gln Ala Leu Tyr Phe Ser Asp Phe Val Cys Gln Cys Pro Glu

Gly Phe Ala Gly Lys Cys Cys Glu Ile Asp Thr Arg Ala Thr Cys Tyr Glu Asp Gln

Gly Ile Ser Tyr Arg Gly Thr Trp Ser Thr Ala Glu Ser Gly Ala Glu Cys Thr Asn Trp
100

Asn Ser Ser Ala Leu Ala Gln Lys Pro Tyr Ser Gly Arg Arg Pro Asp Ala Ile Arg

Leu Gly Leu Gly Asn His Asn Tyr Cys Arg Asn Pro Asp Arg Asp Ser Lys Pro Trp
150

Cys Tyr Val Phe Lys Ala Gly Lys Tyr Ser Ser Glu Phe Cys Ser Thr Pro Ala Cys

Ser Glu Gly Asn Ser Asp Cys Tyr Phe Gly Asn Gly Ser Ala Tyr Arg Gly Thr His

Ser Leu Thr Glu Ser Gly Ala Ser Cys Leu Pro Trp Asn Ser Met Ile Leu Ile Gly Lys
200

Val Tyr Thr Ala Gln Asn Pro Ser Ala Gln Ala Leu Gly Leu Gly Lys His Asn Tyr

Cys Arg Asn Pro Asp Gly Asp Ala Lys Pro Trp Cys His Met Leu Lys Asn Arg Arg
250

Leu Thr Trp Glu Tyr Cys Asp Val Pro Ser Cys Ser Thr Cys Gly Leu Arg Gln Tyr

Ser Gln Pro Gln Phe Arg Ile Lys Gly Gly Leu Phe Ala Asp Ile Ala Ser His Pro Trp

Gln Ala Ala Ile Phe Ala Lys His Arg Arg Ser Pro Gly Glu Arg Phe Leu Cys Gly
300

Gly Ile Leu Ile Ser Ser Cys Trp Ile Leu Ser Ala Ala His Cys Phe Gln Glu Arg Phe

Pro Pro His His Leu Thr Val Ile Leu Gly Arg Thr Tyr Arg Val Val Pro Gly Glu Glu

Glu Gln Lys Phe Glu Val Glu Lys Tyr Ile Val His Lys Glu Phe Asp Asp Asp Thr
350

Tyr Asp Asn Asp Ile Ala Leu Leu Gln Leu Lys Ser Asp Ser Ser Arg Cys Ala Gln

Glu Ser Ser Val Val Arg Thr Val Cys Leu Pro Pro Ala Asp Leu Gln Leu Pro Asp
400

Trp Thr Glu Cys Glu Leu Ser Gly Tyr Gly Lys His Glu Ala Leu Ser Pro Phe Tyr

Ser Glu Arg Leu Lys Glu Ala His Val Arg Leu Tyr Pro Ser Ser Arg Cys Thr Ser

Gln His Leu Leu Asn Arg Thr Val Thr Asp Asn Met Leu Cys Ala Gly Asp Thr Arg
450

Ser Gly Gly Pro Gln Ala Asn Leu His Asp Ala Cys Gln Gly Asp Ser Gly Gly Pro

Leu Val Cys Leu Asn Asp Gly Arg Met Thr Leu Val Gly Ile Ile Ser Trp Gly Leu
500

Gly Cys Gly Gln Lys Asp Val Pro Gly Val Tyr Thr Lys Val Thr Asn Tyr Leu Asp

Trp Ile Arg Asp Asn Met Arg Pro
527

FIG. 1

ACIDIC FORMULATIONS OF T-PA

This is a continuation of copending application Ser. No. 06/862,774 filed on May 13,1986.

The present invention relates to tissue plasminogen activator and in particular to pharmaceutical formulations containing tissue plasminogen activator, their preparation, and their use in human and veterinary medicine.

It is believed that there is a dynamic equilibrium between the enzyme system capable of forming blood clots—the coagulation system—and the enzyme system capable of dissolving blood clots—the fibrinolytic system—which maintains an intact patent vascular bed. To limit loss of blood from injury, blood clots are formed in the injured vessels. After natural repair of the injury, the superfluous blood clots are dissolved through operation of the fibrinolytic system. Occasionally, blood clots form without traumatic injury and may lodge in major blood vessels resulting in a partial or even total obstruction to blood flow. When this occurs in the heart, lung or brain, the result may be a myocardial infarction, pulmonary embolism or stroke. These conditions combined are the leading cause of morbidity and mortality in the industrialised nations.

Blood clots consist of a fibrous network that is capable of dissolution by the proteolytic enzyme, plasmin. The enzyme is derived from the inactive proenzyme, plasminogen, a component of blood plasma, by the action of a plasminogen activator. There are two immunologically distinct mammalian plasminogen activators. Intrinsic plaminogen activator, also known as urokinase, is an enzyme produced by the kidney and can be isolated from urine. It can also be prepared from a number of tissue culture sources. Extrinsic plasminogen activator, also known as vascular plasminogen activator and as tissue plasminogen activator (t-PA), can be isolated from many tissue homogenates (notably human uterus), the vascular cell wall and from some cell cultures. In addition to these two kinds of plasminogen activator, there is also a bacterial product, streptokinase, prepared from beta-haemolytic streptococci. A major drawback with both urokinase and streptokinase is that they are active throughout the circulation and not just at the site of a blood clot. They can, for example, destroy other blood proteins, such as fibrinogen, prothrombin, factor V and factor VIII so reducing blood clotting ability and increasing the risk of haemorrhage. In contrast, the biological activity of T-PA is dependent on the presence of fibrin to which it binds and where it is activated. Maximum activity is thus developed only at the site of a blood clot, i.e. in the presence of the fibrin network to be dissolved, and this greatly avoids the risk of haemorrhage. The main route of t-PA is by intravascular infusion, thus requiring the formulation of t-PA as a parenteral solution. It is generally desirable that a parenteral solution contains a high concentration of drug. This is because the physician or veterinarian can then obtain the required concentration in any given situation simply by dilution of the solution with additional solvent or medium. In addition, it is inadvisable to administer a large volume of solution to a patient with a cardiac or renal disorder since it would put the heart or kidneys under even greater stress. The volume should therefore be kept to a minimum by using a more concentrated formulation. At the same time, any such parenteral solution should be stable in the sense that there is no significant tendency for the drug to be precipitated out of solution either on storage or during any dilution operation.

A number of parenteral solutions of t-PA have been described in general terms in EP-A-41 766, EP-A-93 619, EP-A-112 122, EP-A-113 319, EP-A-123 304, Japanese patent publication 57-120523 (application 56-6936) and Japanese patent publication 58-65218 (application 56-163145). The formulations are aqueous saline solutions of t-PA, in which the pH is about neutral, and suffer from the disadvantage that the solubility of t-PA in such solutions is low in the absence of an increase in the ionic concentration. Consequently, the formulations either contain low concentrations of t-PA, necessitating in some situations the administration of undesirably large volumes of solution to a patient, or they are hypertonic, which on administration may be detrimental to red blood cells.

It has now been found that the solubility of t-PA in an aqueous parenteral solution can be improved if the pH of the solution is within ad acidic range, and that, on administration, the acidity of such a solution presents no significant physiological problems. Accordingly, the present invention provides an aqueous parenteral solution of t-PA, in which the pH is from 2 to 5.

As a result of the improved solubility of t-PA, the parenteral solution of the present invention is capable of achieving high concentrations of t-PA without any substantial risk of the t-PA being precipitated out of solution. In addition, it has been found that the concentration of t-PA in such a solution can readily be reduced by dilution with water of neutral or acidic pH again without any substantial risk of the t-PA being precipitated. The present invention, therefore, provides a stable parenteral solution that allows for greater flexibility in its handling and use by physicians and veterinarians.

The t-PA of use with the present invention may be any bioactive protein substantially corresponding to mammalian, and especially human, t-PA and includes forms with and without glycosylation. It may be one- or two-chain t-PA, or a mixture thereof, as described in EP-A-112 122 and, in the case of fully glycosylated human t-PA, has an apparent molecular weight on polyacrylamide gels of about 70,000 and an isoelectric point of between 7.5 and 8.0. Preferably the t-PA has a specific activity of about 500,000IU/mg (International Units/mg, the International Unit being a unit of activity as defined by WHO, National Institute for Biological Standards and Control, Holly Hill, Hampstead, London, NW3 6RB, U.K.).

The amino acid sequence of tPA preferably substantially corresponds to that set forth in FIG. 1. The sequence is thus identical to that in FIG. 1 or contains one or more amino acid deletions, substitutions, insertions, inversions or additions of allelic origin or otherwise, the resulting sequence having at least 80%, and preferably 90%, homology with the sequence in FIG. 1 and retaining essentially the same biological and immunological properties of the protein. In particular, the t-PA sequence is identical to that in FIG. 1 or has the same sequence but with the amino acid in the 245th position from the serine N-terminus being valine instead of methionine, either sequence optionally being without any of the first three amino acids or optionally having an additional polypeptide N-terminal presequence of Gly-Ala-Arg.

BRIEF DESCRIPTION OF THE DRAWINGS

FIG. 1 sets forth a t-PA amino acid sequence which has thirty-five cysteine residues and thus the potential for forming seventeen disulphide bridges.

In FIGS. 1 and 2, the conventional one and three letter codes have been employed for the amino acid residues as follows:

Figure 2:
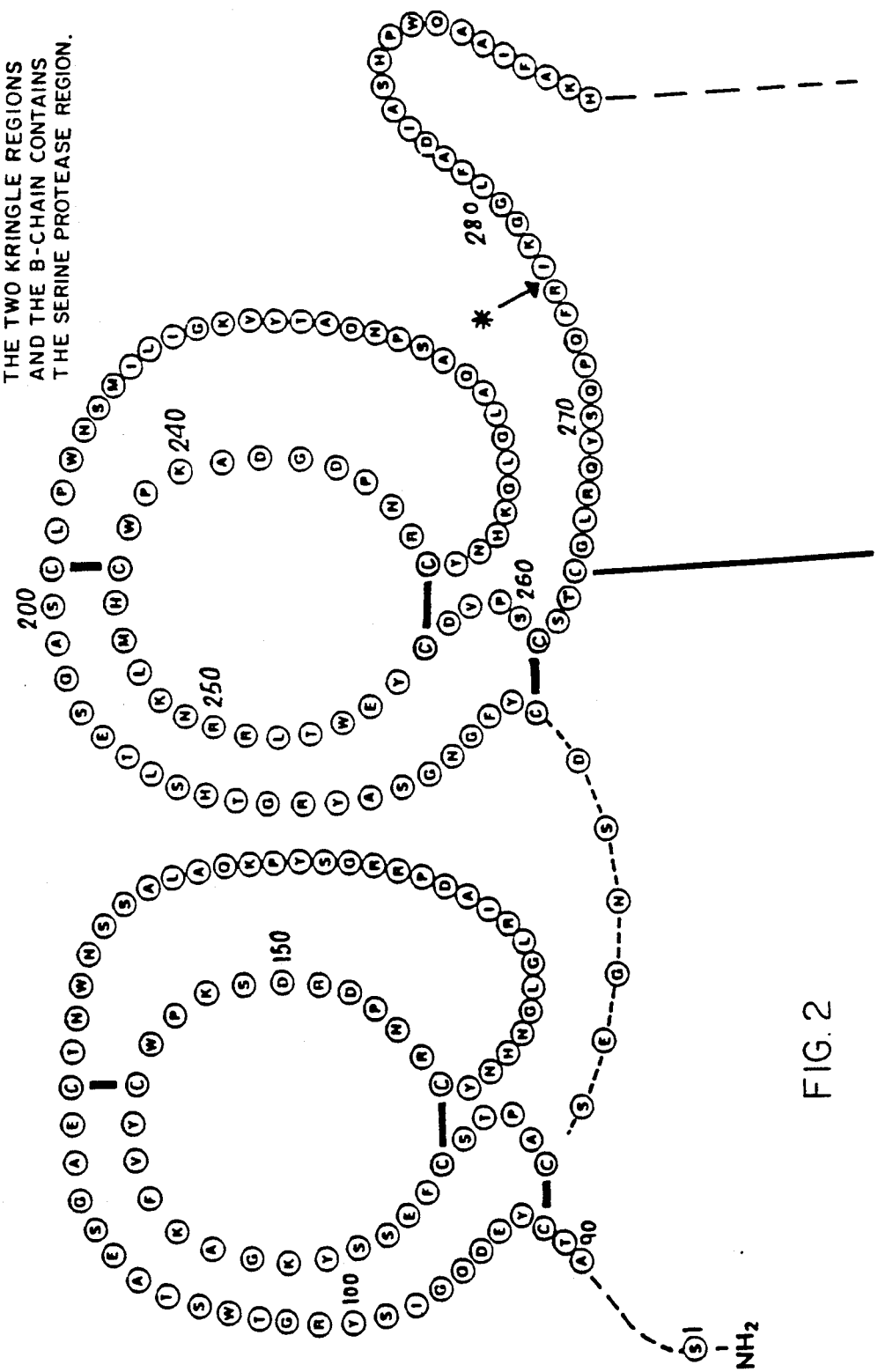
FIGS. 2-2A show, analogy with other proteins whose structure has been determined in more detail, the postulated structure for the tPA sequence (arising from disulphide bond formation) between the amino acid in the 90th position and the proline C-terminus. The structure of the N-terminal region is less certain although some proposals have been put forward (*progress in Fibrinolysis*, 1983, 6, 269-273; and *Proc. Natl. Acad. Sci.*, 1984, 81, 5355-5359). The most important features of the structure of tPA are the two kringle regions (between the 92nd and 173rd amino acids and between the 180th and 261st amino acids), which are responsible for the binding of the protein to fibrin, and the serine protease region, which comprises the major part of the B-chain and which is responsible for the activation of plasminogen. The amino acids of special significance in serine proteases are the catalytic triad, His/Asp/Ser. In t-PA these occur at the 322nd, the 371st and the 463rd positions. The disulphide bridge between the 264th and 395th cysteine amino acid residues is also important in that it holds together the A and B-chains in the two-chain form of t-PA.
Figure 2A:
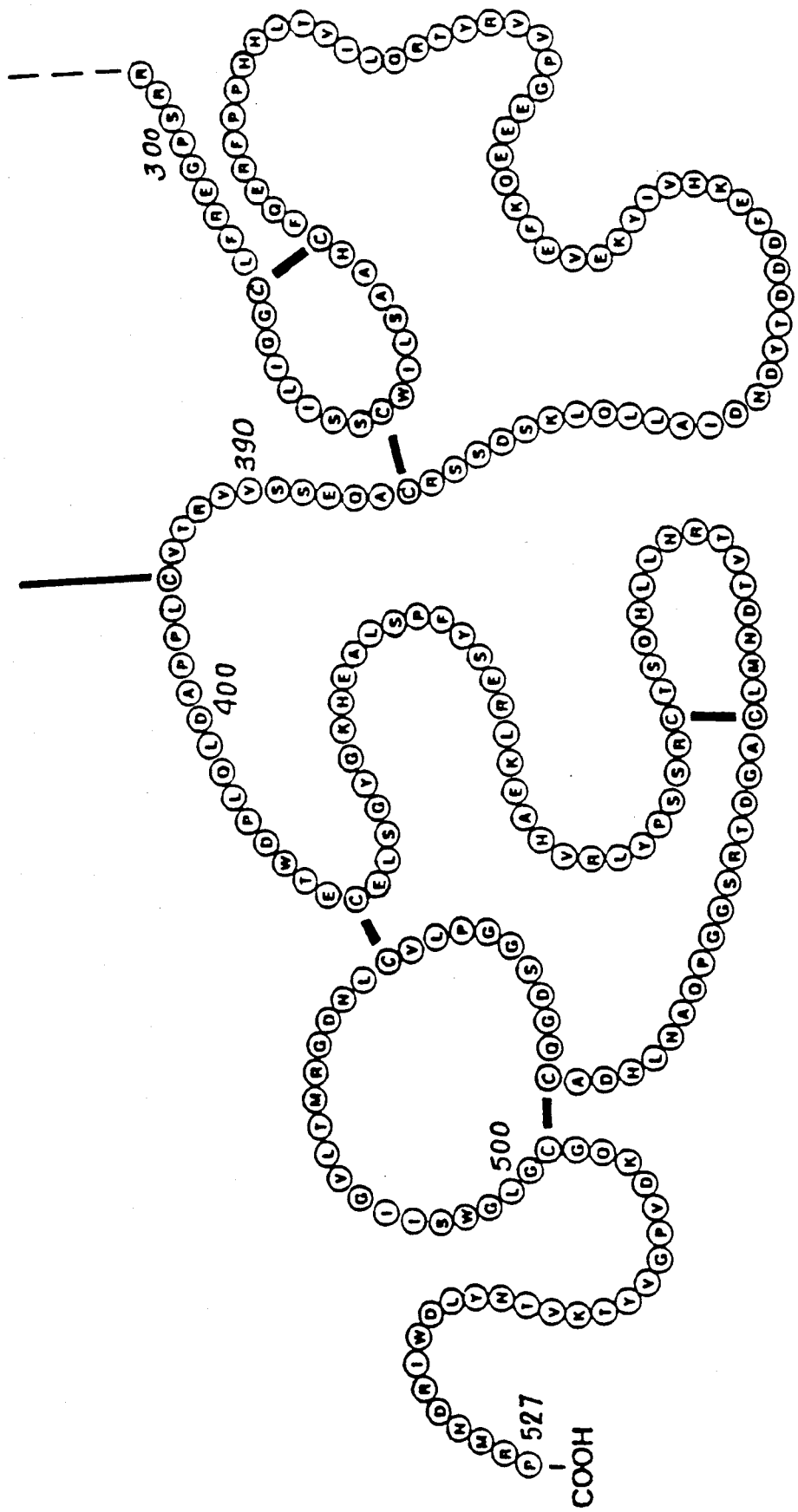

| Asp | D | Aspartic acid | Ile | I | Isoleucine |
|-----|---|---------------|-----|---|------------|
| Thr | T | Threonine | Leu | L | Leucine |
| Ser | S | Serine | Tyr | Y | Tyrosine |
| Glu | E | Glutamic acid | Phe | F | Phenylalanine |
| Pro | P | Proline | His | H | Histidine |
| Gly | G | Glycine | Lys | K | Lysine |
| Ala | A | Alanine | Arg | R | Arginine |
| Cys | C | Cysteine | Trp | W | Tryptohan |
| Val | V | Valine | Gln | Q | Glutamine |
| Met | M | Methionine | Asn | N | Asparagine |

The t-PA may be obtained by any of the procedures described or known in the art. For example, it may be obtained from a normal or neoplastic cell line of the kind described in *Biochimica et Biophysica Acta*, 1979, 580, 140-153; EP-A-41 766 or EP-A-113 319. It is preferred, however, that T-PA is obtained from a cultured transformed or transfected cell line, derived using recombinant DNA technology as described in, for example, EP-A-93 619; EP-A-117 059 or EP-A-117 060. It is particularly preferred that Chinese hamster ovary (CHO) cells are used for the production of t-PA and are derived in the manner as described in *Molecular and Cellular Biology*, 1985, 5(7), 1750-1759. In this way, the cloned gene is cotransfected with the gene encoding dihydrofolate reductase (dhfr) into dhfr⁻CHO cells. Transformants expressing dhfr are selected on media lacking nucleosides and are exposed to increasing concentrations of methotrexate. The dhfr and t-PA genes are thus coamplified leading to a stable cell line capable of expressing high levels of t-PA.

The t-PA is, preferably, purified using any of the procedures described or known in the art, such as the procedures described in *Biochimica et Biophysica Acta*, 1979, 580, 140-153; *J. Biol. Chem.*, 1979, 254(6), 1998-2003; ibid, 1981, 256(13), 7035-7041; *Eur. J. Biochem.*, 1983, 132, 681-686; EP-A-41 766; EP-A-113 319 or GB-A-2 122 219.

There does not appear to be any upper limit on the solubility of t-PA in the parenteral solution. At very high concentrations, such as greater than 150,000,000IU/ml (International Units/ml), the solution merely becomes viscous without any significant precipitation of the t-PA. The concentration of t-PA in the parenteral solution may therefore vary within wide limits, for example from 50,000 to 50,000,000IU/ml. In order to secure the maximum advantage from the present invention, it is preferred that the concentration of t-PA is greater than 100,000IU/ml, more especially greater than 500,000IU/ml, and most especially greater than 1,000,000IU/ml. It is most particularly preferred that the concentration of t-PA is about 5,000,000IU/ml.

The upper limit of the pH of the parenteral solution is, preferably, 4.5. In fact, the pH is, preferably, within the range from 2.5 to 4.0, more preferably from 2.8 to 3.5, and most preferably about 3.0. The desired pH of the parenteral solution is conveniently obtained using a physiologically acceptable inorganic or organic acid. Examples of such an acid include hydrochloric acid, sulphuric acid and nitric acid, and citric acid, tartaric acid and benzenesulphonic acid. Of these examples, hydrochloric acid is preferred.

Although some physiologically acceptable co-solvent may optionally be present in addition to water, it is preferred that the medium for the parenteral solution is wholly or substantially aqueous.

The parenteral solution may be hypertonic, hypotonic or isotonic with the blood serum of the patient. To avoid undesirable side effects, however, the parenteral solution is, preferably, isotonic although minor deviations are not of great physiological concern. A substantially isotonic parenteral solution may be obtained by the inclusion of a physiologically acceptable agent that is capable of raising the tonicity of the solution to the required level. Examples of such an agent are well known in the art and include dextrose (in anhydrous or monohydrate form) and sodium chloride and mixtures thereof. The concentration of the agent in the parenteral solution will, of course, vary from agent to agent. In the case of sodium chloride, the concentration is preferably from 7 to 10 mg/ml, and most preferably about 8.5 mg/ml, the concentration often referred to as physiological saline solution or just physiological saline. In the case of anhydrous dextrose, the concentration is preferably from 30 to 70 mg/ml, and most preferably about 50 mg/ml. In the event that the concentration of t-PA in a substantially isotonic parenteral solution is required to be reduced, it is preferred to carry out the dilution with an aqueous solution of the same agent at the same concentration so as to maintain a substantially isotonic solution.

The parenteral solution may optionally contain additives normally associated with formulations of this type. Examples include human serum albumin. In addition, t-PA has a tendency to adsorb to glass and plastic surfaces and, therefore, it may be desirable to include a surface active agent in the parenteral solution to prevent or minimise such adsorption. Examples of such an agent include polyoxyethylene derivatives of fatty acid partial esters of sorbitol anhydrides, such as that marketed under the trade name "Tween 80".

One of the surprising advantages of the present invention, apart from the substantially increased solubility of t-PA, is that the use of an acidic parenteral solution having a pH within the limits as defined herein does not appear to present any significant adverse physiological effects on administration to the patient. It would seem that the bloodstream is generally able to raise the pH of the solution to neutral almost as soon as contact is made, the t-PA being rapidly distributed within the bloodstream. It is, however, preferred that this process is not substantially impeded in any way and that the parenteral solution does not contain a strong buffering agent. A weak buffering agent, though, that does not significantly inhibit this process may be included and, indeed, at acidic pH t-PA itself acts as its own weak buffering agent. In addition, human serum albumin is capable of acting as weak buffering agent.

Because of the substantially increased solubility of t-PA in the parenteral solution of the present invention, there is no need to include any additional material, such as lysine or ornithine or a salt thereof, for enhancing the solubility of t-PA.

The parenteral solution may be prepared in accordance with conventional pharmaceutical formulation procedures and techniques using t-PA in the form of a purified solution or solid. The present invention, therefore, provides a process for preparing an aqueous parenteral solution of t-PA, as defined herein, which comprises:

(k) obtaining a purified solution of t-PA and exchanging the medium for an aqueous medium having a pH from 2 to 5; or (ii) dissolving t-PA in an aqueous medium having a pH from 2 to 5; and sterilizing the resulting solution.

The purification of t-PA may involve as a final stage the elution of the protein from a chromatographic column as a solution containing a strong buffering agent. As mentioned previously, it is preferred that the parenteral solution does not contain a strong buffering agent and, therefore, a convenient means for effecting its removal whilst exchanging the medium is to use dialysis. This may be carried out using dialysis tubing or an artificial kidney in which the purified solution is dialysed against an aqueous medium in which the pH is from 2 to 5. It may be desirable, especially if the concentration of t-PA in the purified solution is high, first to adjust the pH of the solution so that it is from 2 to 5. Another means for effecting the removal of a strong buffering agent whilst exchanging the medium is to subject the purified solution to gel filtration and to develop the column with an aqueous medium in which the pH is from 2 to 5.

t-PA in the form of a precipitated solid may, preferably, be obtained from a purified solution by adjusting the pH to about 5.5, cooling the solution to just above its freezing point, and recovering the protein by, for example, centrifugation. The precipitated solid may then be dissolved in an aqueous medium having a pH from 2 to 5 in a conventional manner.

The sterilization of the resulting solution may be carried out conventionally, for example, by filter sterilization.

The parenteral solution is normally presented in sealed, sterile, plastic or glass containers. It may also be presented in unit-dosage forms, such as in ampoules, vials or disposable injection devices, or in multi-dosage forms, such as in infusion bags or bottles. The volume of solution to be presented in such containers may vary widely but, conveniently, si from 0.5 to 20 ml.

In order to stabilise the t-PA, the parenteral solution is, preferably, frozen and kept at $-10°$ to $-30°$ C.

The biological activity of t-PA in dissolving the fibrin network of blood clots has led to its utility in the treatment of thrombotic disorders (The Lancet, Nov. 7th 1981, 1018-1020; ibid., Apr. 13th 1985, 842-847; *The New England Journal of Medicine*, 1984, 310(10), 609-613; and ibid., 1985, 312(14), 932-936). The present invention, therefore, provides a method for the treatment of a thrombotic disorder in a mammal, which comprises the administration to the mammal of an aqueous parenteral solution of t-PA, as defined herein. In the alternative, there is also provided an aqueous parenteral solution of t-PA, as defined herein, for use in human or veterinary medicine, especially for use in the treatment of a thrombotic disorder.

Particular examples of a thrombotic disorder are known in the art but include myocardial infarction, deep vein thrombosis, pulmonary embolism and stroke.

The main route of administration of the parenteral solution is by intravascular, especially intravenous, infusion although conceivably other routes of administration, such as intramuscular administration, may be employed. Intravascular infusions are normally carried out with the parenteral solution contained within an infusion bag or bottle or within an electrically operated infusion syringe. The solution may be delivered from the infusion bag or bottle to the patient by gravity feed or by the use of an infusion pump. The use of gravity feed infusion systems does not afford sufficient control over the rate of administration of the parenteral solution and, therefore, the use of an infusion pump is preferred especially with solutions containing relatively high concentrations of t-PA. More preferred, however, is the use of an electrically operated infusion syringe which offers even greater control over the rate of administration.

An effective amount of t-PA to treat a mammal with a thrombotic disorder will of course depend upon a number of factors including, for example, the age and weight of the mammal, the precise condition requiring treatment and its severity, the route of administration, and will ultimately be at the discretion of the attendant physician or veterinarian. It is likely, however, that an effective amount for lysing a coronary artery thrombus, for example, will generally be in the range from 150,000 to 450,000IU/kg bodyweight of patient per hour. Thus, for a 70 kg adult human being, an effective amount per hour will generally be from 10,000,000 to 30,000,000IU, especially about 20,000,000IU, and this amount may be administered with or without a priming dose. It is also likely that the dosage will be less for some thrombotic conditions, such as deep vein thrombosis and acute stroke, or for simply maintaining patency of an already reperfused coronary artery. In these situations, an effective amount will generally be from 7,000 to 36,000IU/kg bodyweight of patient per hour.

The following examples are provided in illustration of the present invention and should not be construed in any way as constituting a limitation thereof.

EXAMPLE 1

A clarified harvest of t-PA, obtained from a cultured transformed CHO cell line which was derived using the procedure of *Molecular and Cellular Biology*, 1985, 5(7), 1750-1759, was purified chromatographically and the t-PA collected as an aqueous solution containing 0.1M sodium citrate and 0.01% (w/v) Tween 80 at a pH of 5.5. The pH of the solution was adjusted to 3.0 with hydrochloric acid and the resulting solution concentrated by ultrafiltration using an H-10 Cartridge (Amicon Ltd., Upper Mill, Stonehouse, Gloucestershire, England). A concentrated, purified aqueous solution of t-PA (2,500,000IU/ml), containing 0.1M sodium citrate, 0.23M sodium chloride (arising from the addition of hydrochloric acid) and 0.01% (w/v) Tween 80 and having a pH of 3.0, was thus obtained. This solution was placed in dialysis tubing having a molecular weight cut-off of about 14,000 and dialysed at 4° C. against four changes of 50 volumes of filter-sterilized, physiological saline (0.85% (w/v) sodium chloride) containing 0.01% (w/v) Tween 80 and adjusted to pH 3.0 with concentrated hydrochloric acid. Each dialysis step was allowed to proceed for 12 hours. Following recovery of the aqueous solution from the dialysis bag, it was filter-sterilized and diluted with physiological saline to contain 500,000IU/ml of t-PA. The resulting parenteral solution was then filled into glass vials which were sealed and frozen and stored at −20° C.

EXAMPLE 2

A clarified harvest of t-PA, obtained from a cultured transformed CHO cell line which was derived using the procedure of *Molecular and Cellular Biology*, 1985, 5(7), 1750-1759, was purified chromatographically and the t-PA collected as an aqueous solution containing 0.17M sodium citrate and 0.01% (w/v) Tween 80 at a pH of 5.5. The pH of the solution was adjusted to 3.0 with hydrochloric acid and the resulting solution concentrated by ultrafiltration using an H-10 Cartridge (Amicon Ltd., Upper Hill, Stonehouse, Gloucestershire, England). The concentrated aqueous solution was further purified by applying it to a gel filtration column (Sephadex G-150; Pharmacia Biotechnology, Uppsala, Sweden) and eluting with 0.85% saline solution containing 0.01% (w/v) Tween 80 at a pH of 3.0. A highly purified aqueous solution of t-PA was thus obtained which was concentrated once more using a disposable artificial kidney. The t-PA was precipitated out of solution by increasing the pH to 5.5 with sodium hydroxide and maintaining the suspension at 4° C. for 2 hours. The t-PA was recovered by centrifugation at 4000×g for 30 minutes at 4° C. The pellet of t-PA was redissolved in an aqueous solution of sodium chloride (0.85% (w/v)) containing 0.01% (w/v) Tween 80 and adjusted to pH 3.0 with hydrochloric acid. The volume of saline solution used was that required to give a concentration of t-PA between 7,500,000IU/ml and 10,000,000IU/ml. This solution of t-PA was diluted with further aqueous solution of sodium chloride (0.85% (w/v)) containing 0.01% (w/v) Tween 80 and adjusted to pH 3.0 with hydrochloric acid, and also with sufficient of a solution of 10% (w/v) mannitol in the same acid saline solution to give final concentrations of 5,000,000IU/ml of t-PA and 25 mg/ml of mannitol. The resulting solution was filter sterilized and dispensed in volumes of 1 ml into glass vials which were frozen and stored at −20° C.

EXAMPLE 3

The thrombolytic efficacy of the parenteral solution of Example 1 was evaluated in an in vivo model of jugular vein thrombosis.

(a) Procedure

The experimental procedure essentially followed that described by Collen et al (*J. Clin. Invest.*, 1983, 71, 368-376).

The parenteral solution of Example 1 was allowed to thaw and diluted with sterile isotonic saline adjusted to pH 3.0 containing 0.01% Tween 80 to provide sufficient solution for a 2 hour infusion of 500,000IU/kg of t-PA. Infusion was via a cannula in the right femoral vein. Three New Zealand white rabbits were used in the study. After infusion the degree of thrombolysis was estimated.

(b) Results

The percentage thrombolysis was 22.3±4.2 thus demonstrating the thrombolytic effect of the parenteral solution of Example 1. In addition, there were no adverse reactions observed with the infusion of this solution.

I claim:

1. A sterilized unbuffered aqueous parenteral solution of t-PA substantially corresponding to human t-PA, in which the pH is from 2 to 5.

2. A parenteral solution according to claim 1, wherein the t-PA has the amino acid sequence set forth in FIG. 1 or has the same amino acid sequence but with the amino acid in the 245th position from the serine N-terminus being valine instead of methionine.

3. A parenteral solution according to claim 1, wherein the t-PA is obtained from cultured transformed or transfected cell line derived using recombinant DNA technology.

4. A parenteral solution according to claim 1, wherein the concentration of t-PA is greater than 100,000IU/ml.

5. A parenteral solution according to claim 4, wherein the concentration of t-PA is greater than 500,000IU/ml.

6. A parenteral solution according to claim 1, wherein the concentration of t-PA is greater than 1,000,000IU/ml.

7. A parenteral solution according to claim 6, wherein the concentration of t-PA is about 5,000,000IU/ml.

8. A parenteral solution according to claim 1, wherein the pH is from 2 to 4.5.

9. A parenteral solution according to claim 8, wherein the pH is from 2.5 to 4.0.

10. A parenteral solution according to claim 9, wherein the pH is from 2.8 to 3.5.

11. A parenteral solution according to claim 10, wherein the pH is about 3.0.

12. A parenteral solution according to claim 1, which contains a physiologically acceptable agent that renders the solution substantially isotonic with human blood serum.

13. A parenteral solution according to claim 12, wherein the physiologically acceptable agent is saline.

14. A parenteral solution according to claim 12, wherein the physiologically acceptable agent is dextrose.

15. A parenteral solution according to claim 1, which contains a surface active agent.

16. A sterilized unbuffered aqueous saline parenteral solution of t-PA, in which the pH is from 2 to 5.

17. A method for the treatment of a thrombotic disorder in a mammal having said disorder which comprises the intravascular administration to said mammal of a parenteral solution according to claim 16.

18. A sealed container of a parenteral solution according to claim 1.

19. A sealed container of a parenteral solution according to claim 16.

20. A sealed sterile container containing a sterilized unbuffered aqueous parenteral solution of t-PA in which the pH is from 2 to 5 and the t-PA is substantially in the form of t-PA native to human tissue.

21. The container of claim 20 in which the solution is isotonic.

22. A method of treating a human having a thrombotic disorder comprising intravascularly infusing said human with a sterile unbuffered solution of t-PA substantially in a form native to human tissue in which the pH is from 2 to 5.

23. The method of claim 22 in which the solution is isotonic.

24. A method of treating a human having a thrombotic disorder comprising the intravenous infusion to said human of a sterile unbuffered solution of t-PA substantially in the form of t-PA native to human tissue in which the pH is from 2 to 5.

25. The method of claim 24 in which the solution is isotonic.

26. A sterile container having a solution consisting of an unbuffered aqueous parenteral solution of t-PA substantially corresponding to human t-PA, in which the pH is from 2 to 5 and the concentration of t-PA is greater than 100,000IU/ml.

27. The container according to claim 26, in which the concentration of t-PA is greater than 500,000IU/ml.

28. The container according to claim 26, in which the concentration of t-PA is greater than 1,000,000IU/ml.

29. The container according to claim 26, in which the concentration of t-PA is greater than 5,000,000IU/ml.

30. The container according to claim 26, in which the concentration of t-PA is greater than 100,000IU/ml to 50,000,000IU/ml.

31. The container according to claim 26, in which the solution does not include lysine, ornithine or salts thereof.

* * * * *